United States Patent
An et al.

(10) Patent No.: US 11,644,424 B2
(45) Date of Patent: May 9, 2023

(54) INTERFEROMETRIC METHOD AND APPARATUS FOR NON-INVASIVE ASSESSMENT OF OOCYTE MATURITY AND COMPETENCY

(71) Applicant: Animated Dynamics, Inc., Indianapolis, IN (US)

(72) Inventors: Ran An, Indianapolis, IN (US); Gayatri Narayanan, Indianapolis, IN (US); Travis A. Morgan, Indianapolis, IN (US); Theodore R. Schenberg, Indianapolis, IN (US)

(73) Assignee: Waverly Industries, LLC, Culver, IN (US)

( * ) Notice: Subject to any disclaimer, the term of this patent is extended or adjusted under 35 U.S.C. 154(b) by 346 days.

(21) Appl. No.: 16/859,537

(22) Filed: Apr. 27, 2020

(65) Prior Publication Data
US 2020/0340926 A1     Oct. 29, 2020

Related U.S. Application Data

(60) Provisional application No. 62/839,925, filed on Apr. 29, 2019.

(51) Int. Cl.
*G01N 21/84* (2006.01)
*G01N 21/47* (2006.01)
(Continued)

(52) U.S. Cl.
CPC ............. *G01N 21/84* (2013.01); *G01N 21/47* (2013.01); *G01N 21/55* (2013.01);
(Continued)

(58) Field of Classification Search
CPC .......... G01N 15/147; G01N 2015/149; G01N 15/14; G01N 21/17; G01N 33/5005;
(Continued)

(56) References Cited

U.S. PATENT DOCUMENTS

| | | | |
|---|---|---|---|
| 6,020,963 A * | 2/2000 | DiMarzio | G01N 21/4795 356/491 |
| 7,522,282 B2 | 4/2009 | Nolte et al. | |

(Continued)

FOREIGN PATENT DOCUMENTS

| | | | |
|---|---|---|---|
| FR | 2814247 A1 * | 3/2002 | G02B 21/0032 |
| JP | 2004512516 A * | 4/2004 | |

(Continued)

OTHER PUBLICATIONS

International Search Report and Written Opinion of the International Searching Authority, PCT/US2020/030082, dated Sep. 16, 2020, 12 pages.

*Primary Examiner* — Michael P Stafira
(74) *Attorney, Agent, or Firm* — Bose McKinney & Evans LLP

(57) ABSTRACT

An interferometric method and apparatus for the non-invasive assessment of oocyte maturity and competency. The method includes placing an oocyte in a sample holder to provide a biological target; generating a near infrared light; using a beam splitter to split the near infrared light into a signal light portion and a reference light portion; projecting the signal light portion onto the biological target; collecting reflected and back scattered light from the signal light portion projected onto the biological target with a detector; collecting at least a portion of the reference light portion with the detector; generating interferometric image data based upon the collected signal and reference light; and assessing the maturity of the oocyte based upon the interferometric data while maintaining the viability of the oocyte. When the oocyte is part of a cumulus-oocyte complex, the assessment is accomplished without removing cumulus cells from the cumulus-oocyte complex while maintaining viability.

21 Claims, 12 Drawing Sheets

(51) Int. Cl.
*G01N 33/50* (2006.01)
*G01N 21/55* (2014.01)
(52) U.S. Cl.
CPC ... *G01N 33/5005* (2013.01); *G01N 2201/062* (2013.01); *G01N 2201/08* (2013.01)
(58) Field of Classification Search
CPC ....... G01N 2015/1006; G01N 15/1404; G01N 15/1459; G01N 15/1468; G01N 2015/0065; G01N 2015/1406; G01N 2015/1415; G01N 2021/6439; G01N 21/63; G01N 21/6428; G01N 33/48; G01N 21/453; G01N 21/55; G01N 15/1475; G01N 15/1434; G01N 15/1463; G01N 2015/1454; G01N 21/47; G01N 21/84; G01N 21/8806; G01N 2201/062; G01N 2201/08; G01N 33/5044; G01N 33/5091; G01N 33/689; G01N 2021/8829; G01N 2021/8848; G01N 21/88; G01N 2021/8816; G01N 2021/8825; G01N 2021/8835; G01N 2021/8845; G01N 2333/4712; G01N 2015/1497; G01N 2015/1493; G01N 15/10; G01N 2015/1087; G01N 2015/1093; G01N 33/4833; G01N 33/6803; G01N 2500/10; G01N 33/532; G01N 33/582; G01N 33/085; G01N 2035/1034; G01N 2800/367; G01N 33/5023; G01N 1/38; G01N 2035/00356; G01N 2035/00376; G01N 2035/00396; G01N 2035/00752; G01N 2035/1025; G01N 33/08; G01N 35/00732; G01N 35/028; G01N 35/1002; G01N 35/1004; G01N 35/1016; G01N 35/1074; G01N 15/1436; G01N 33/58; G01N 33/487; G01N 33/4915; G01N 33/5011; G01N 33/5088; G01N 33/6872; G01N 2333/726; G01N 2500/04; G01N 33/542; G01N 21/3577; G01N 35/00584; G01N 1/34; G01N 33/5008; G01N 2800/385; G01N 2800/387; G01N 2500/00; G01N 33/74; G01N 21/35; G01N 21/65; G01N 2201/061; G01N 33/68; G01N 1/42; G01N 21/75; G01N 2021/651; G01N 21/03; G01N 21/0303; G01N 21/33; G01N 21/64; G01N 2333/4603; G01N 2333/515; G01N 2458/15; G01N 33/483; G01N 33/502; G01N 35/0099; G01N 35/10; G01N 21/3563; G01N 2333/9015; G01N 33/5085; G01N 2035/0418; G01N 2333/46; G01N 2570/00; G01N 33/5047; G01N 35/026; G01N 35/1065; G01N 21/31; G01N 21/552; G01N 21/59; G01N 21/951; G01N 2333/82; G01N 33/50; G01N 33/505; G01N 33/5058; G01N 33/54373; G01N 33/6842; G01N 33/6875; G01N 2021/845; G01N 21/6458; G01N 21/85; G01N 2201/125; G01N 2201/129; G01N 2333/70539; G01N 2333/70596; G01N 2800/52; G01N 33/04; G01N 33/5035; G01N 33/5308; G01N 33/56966; G01N 33/6848; G01N 33/6896; G01N 33/948; G01N 1/2806; G01N 1/44; G01N 15/06; G01N 15/1484; G01N 2015/0693; G01N 2021/217; G01N 2021/218; G01N 2021/3155; G01N 2021/656; G01N 2035/00445; G01N 2035/041; G01N 21/21; G01N 21/27; G01N 21/6452; G01N 21/7703; G01N 2800/30; G01N 2800/304; G01N 33/5014; G01N 33/5306; G01N 33/543; G01N 33/56977; G01N 33/57407; G01N 33/57492; G01N 33/6812; G01N 33/6863; G01N 33/6878; G01N 33/92; G01N 33/942; G01N 35/0092; G01N 35/04; G01N 1/4044; G01N 15/00; G01N 2015/0687; G01N 2015/1443; G01N 2015/1447; G01N 2015/1488; G01N 2021/3595; G01N 2021/399; G01N 2021/6419; G01N 2021/6421; G01N 2021/6478; G01N 21/09; G01N 21/314; G01N 21/3581; G01N 21/39; G01N 21/4788; G01N 21/51; G01N 21/53; G01N 2201/06113; G01N 2201/0633; G01N 2201/0635; G01N 2201/0675; G01N 2201/068; G01N 2201/105; G01N 23/06; G01N 2333/43591; G01N 2333/4709; G01N 2333/68; G01N 2333/695; G01N 2333/72; G01N 2333/918; G01N 2800/24; G01N 2800/26; G01N 2800/2835; G01N 29/04; G01N 30/92; G01N 33/2835; G01N 33/5073; G01N 33/53; G01N 33/533; G01N 33/54306; G01N 33/564; G01N 33/566; G01N 33/56972

See application file for complete search history.

(56) References Cited

U.S. PATENT DOCUMENTS

| | | | |
|---|---|---|---|
| 8,072,585 B2 | 12/2011 | Wang et al. | |
| 8,218,152 B1 * | 7/2012 | Marks | G02B 21/0056 356/497 |
| 8,289,522 B2 | 10/2012 | Tearney et al. | |
| 9,829,482 B2 | 11/2017 | An et al. | |
| 10,101,147 B2 | 10/2018 | Nolte et al. | |
| 10,642,014 B2 | 5/2020 | Nolte et al. | |
| 2015/0079621 A1 * | 3/2015 | An | G01N 33/5091 435/29 |
| 2017/0242230 A1 * | 8/2017 | Gareau | G02B 21/0064 |
| 2018/0239950 A1 | 8/2018 | Needleman et al. | |
| 2020/0134773 A1 * | 4/2020 | Pinter | G01N 21/8806 |

FOREIGN PATENT DOCUMENTS

| | | | | |
|---|---|---|---|---|
| KR | 10-2012-0066023 | | 6/2012 | |
| KR | 20150120537 A | * | 10/2015 | |
| KR | 101699604 B1 | * | 1/2017 | |
| WO | WO 2010/151221 A1 | | 12/2010 | |
| WO | WO 2011/025736 A1 | | 3/2011 | |
| WO | WO-2015092019 A1 | * | 6/2015 | ............. A61B 90/37 |
| WO | WO-2016025751 A1 | * | 2/2016 | ......... G02B 21/0024 |
| WO | WO-2016156516 A2 | * | 10/2016 | ......... G01N 21/6428 |
| WO | WO-2018078417 A1 | * | 5/2018 | ......... G01B 9/02007 |

* cited by examiner

INTERFEROMETRIC METHOD AND APPARATUS FOR NON-INVASIVE ASSESSMENT OF OOCYTE MATURITY AND COMPETENCY

CROSS REFERENCE TO RELATED APPLICATIONS

This application claims priority under 35 U.S.C. 119(e) of U.S. provisional patent application Ser. No. 62/839,925 filed on Apr. 29, 2019 entitled INTERFEROMETRIC METHOD AND APPARATUS FOR NON-INVASIVE ASSESSMENT OF OOCYTE MATURITY AND COMPETENCY the disclosure of which is hereby incorporated herein by reference.

BACKGROUND

Conventional in vitro fertilization (IVF) clinical and reproductive research labs lack a non-invasive way to determine if a cumulus-oocyte complex (COC) has matured or not. Instead, in conventional clinics and labs, embryologists denude the COC to remove all the cumulus cells to perform the maturity check. This is necessary because (1) conventional microscopes cannot penetrate deep enough through cumulus cells to have a clear oocyte image; and (2) for other three-dimensional (3D) image methods, such as, confocal microscopy or light sheet microscopy, the light intensity is too high for the COCs to remain healthy. The denude process is irreversible, i.e., once the cumulus cells are removed, they cannot be reattached. Human oocytes cannot mature without the cumulus cells. Thus, for human IVF practice, the irreversible denude process means that any immature oocytes that were denuded will have to be abandoned. In the practice, the number of oocytes is generally very limited, thus, there is a need in IVF field to be able to measure the maturity of COCs without damaging either the oocyte or the cumulus cells.

SUMMARY

Disclosed herein is an apparatus and method using a short-coherence spectral domain interferometer to measure the maturity of living cumulus-ooycte complex (COC) cells and denuded oocytes. The disclosed method is non-invasive and label free. It is capable of determining the maturity of living COCs and oocytes without damage to either the oocyte or the cumulus cells.

The invention comprises, in one form thereof, a method for non-invasively assessing the maturity of an oocyte wherein the method includes placing the oocyte in a sample holder to provide a biological target; generating a near infrared light with a light source; using a beam splitter to split the near infrared light into a signal light portion and a reference light portion; projecting the signal light portion of the near infrared light onto the biological target; collecting reflected and back scattered light from the signal light portion projected onto the biological target with a detector; collecting at least a portion of the reference light portion with the detector wherein the collected reference light has not interacted with the biological target; generating interferometric image data based upon the collected signal and reference light; and assessing the maturity of the oocyte based upon the interferometric data while maintaining the viability of the oocyte.

In some embodiments, the oocyte forming the biological target is part of a cumulus-oocyte complex and assessing of the maturity of the oocyte is accomplished without denuding cumulus cells from the cumulus-oocyte complex while maintaining the viability of the cumulus-oocyte complex.

In some embodiments, the near infrared light generated by the light source has a wavelength within the range of 800 micrometers to 1000 micrometers. For example, the near infrared light generated by the light source may have a wavelength of 850 micrometers.

In some embodiments, the near infrared light generated by the light source has a power of no more than 5 milliwatts and the step of projecting the signal light portion of the near infrared light onto the biological target exposes the biological target to no more than 100 millijoules of energy from the near infrared light.

The light source used to generate the near infrared light may take the form of a superluminescent diode. In some embodiments, the superluminescent diode is coupled with a fiber optic cable and the method further comprises using the fiber optic cable to convey the near infrared light from the superluminescent diode to a location where the light is projected at the beam splitter.

In some embodiments having a superluminescent diode coupled with a fiber optic cable, the superluminescent diode and driving circuitry providing the superluminescent diode with an electrical current to generate the near infrared light are positioned in a first housing that is spaced from and separated from a probe housing, the beam splitter and detector being disposed within the probe housing and wherein the fiber optic cable extends from the first housing to the probe housing and wherein the first housing includes a cooling fan and the probe housing does not include a cooling fan.

In some embodiments, the method further includes the step of providing an objective lens in the path of the signal light between the beam splitter and the biological target. The method may further include the step of providing a pair of galvanometric mirrors which are controllably rotated about a pair of mutually perpendicular axes and positioning the galvanometric mirrors in the path of the signal light between the beam splitter and the objective lens whereby controlled rotation of the galvanometric mirrors can be used to scan the biological target with the signal light.

In some embodiments, the method further includes the step of providing a second image sensor for recording two-dimensional image data.

In some of the embodiments having a second image sensor, the method also includes assessing a plurality of biological targets, the plurality of biological targets being disposed in a plurality of sample holders wherein each individual sample holder has an identifying label affixed thereto, and wherein the method further includes acquiring an image of the identifying label with the second camera when assessing a biological target from the sample holder.

In some of the embodiments having a second image sensor, the method also includes the step of providing an objective lens in the path of the signal light between the beam splitter and the biological target and positioning the second image sensor to acquire two-dimensional image data of the biological target through the objective lens.

In some embodiments, the method further includes providing an objective lens in the path of the signal light between the beam splitter and the biological target; mounting the objective lens, the beam splitter and the detector in a probe housing; positioning the sample holder on a target support; and providing a support structure wherein the probe housing is securable to the support structure at a plurality of different locations whereby the signal light can be directed at the biological target from a plurality of different positions.

The invention comprises in another form thereof, a system for non-invasively assessing the maturity of an oocyte wherein the system includes a superluminescent diode which generates a near infrared light having a wavelength within the range of 800 micrometers to 1000 micrometers; a beam splitter positioned to divide the near infrared light and thereby generate a signal light portion and a reference light portion, the signal light portion being directed at a biological target to generate reflected and back scattered signal light; a reference beam reflector positioned to reflect the reference light portion; a detector positioned to receive the reference light portion reflected by the reference beam reflector and the reflected and back scattered signal light to thereby generate interferometric image data of the biological target.

In some embodiments of the apparatus, the near infrared light generated by the superluminescent diode has a wavelength of 850 micrometers.

In some embodiments of the apparatus, the superluminescent diode is coupled with a fiber optic cable, the fiber optic cable conveying the near infrared light generated by the superluminescent diode to a location where the light is projected at the beam splitter.

In some embodiments of the system having a fiber optic cable, the near infrared light generated by the superluminescent diode has a power of no more than 5 milliwatts as conveyed through the fiber optic cable.

In some embodiments of the system having a fiber optic cable, the system further includes driving circuitry which supplies electrical current to drive the operation of the superluminescent diode, the driving circuitry and the superluminescent diode being disposed in a first housing, the beam splitter, the reference beam reflector and the detector being disposed in a probe housing, the probe housing being separate and spaced apart from the first housing, the fiber optic cable conveying the near infrared light extending between the first housing and the probe housing and emitting the near infrared light within the probe housing.

In some embodiments of the apparatus, the system further includes a pair of galvanometric mirrors controllably rotatable about mutually perpendicular axes wherein the galvanometric mirrors are positioned in the path of the signal light portion between the beam splitter and the biological target; and an objective lens positioned in the path of the signal light portion between the pair of galvanometric mirrors and the biological target.

In some embodiments, the system further includes a second image sensor adapted to record two-dimensional image data.

In some embodiments of the system having a second image sensor, the system may further include a plurality of sample holders, each sample holder being adapted to hold a separate biological target and wherein each sample holder has an identifying label affixed thereto, and wherein the second image sensor is adapted to acquire an image of the identifying label on the sample holder.

In some embodiments of the system having a second image sensor, the system further includes an objective lens positioned between the beam splitter and the biological target and a second light source positioned to illuminate the biological target wherein the second image sensor is positioned to collect light generated by the second light source after the light generated by the second light source has interacted with the biological target and passed through the objective lens to thereby acquire image data of the biological target.

In some embodiments, the system further includes a probe housing and an objective lens wherein the beam splitter, reference beam reflector, objective lens and detector are disposed on the probe housing and wherein the objective lens is positioned in the path of the signal light portion between the beam splitter and the biological target; and a support structure, the support structure comprising a support ring and a target support, the biological target being supportable on the target support, and wherein the probe housing is securable to the support ring at a plurality of different location encircling the target support whereby the signal light can be directed at the biological target from a plurality of different positions.

BRIEF DESCRIPTION OF THE DRAWINGS

The above mentioned and other features of this invention, and the manner of attaining them, will become more apparent and the invention itself will be better understood by reference to the following description of embodiments of the invention taken in conjunction with the accompanying drawings, wherein.

Figure 1:
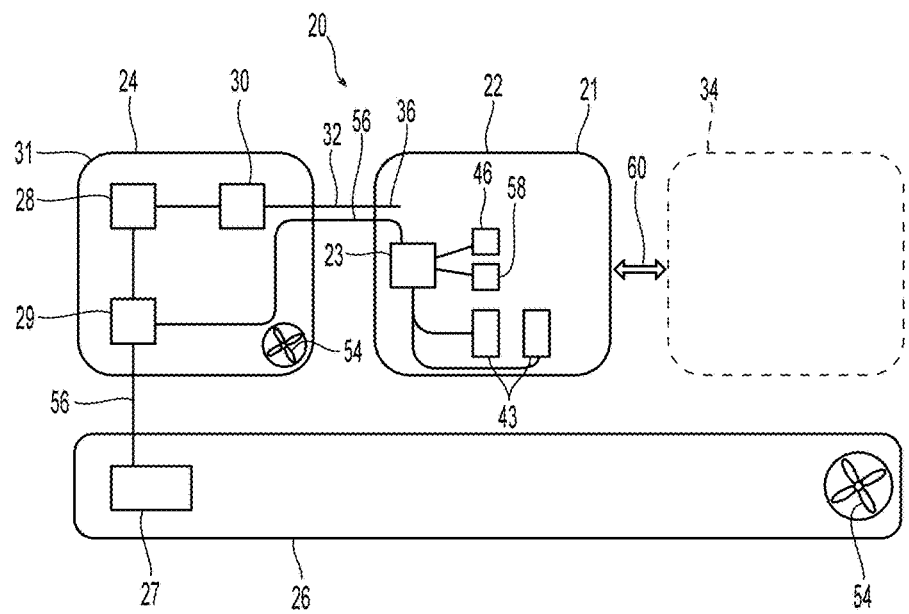
FIG. 1 is a schematic representation of a system for non-invasively assessing the maturity of an oocyte.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise form disclosed.

DETAILED DESCRIPTION

A spectral domain interferometer system 20 is schematically depicted in FIG. 1. In the illustrated embodiment, system 20 includes a probe 22, driver 24 and a personal computer 26. Personal computer 26 may be in communication with a local network and a remote server through a larger network such as the internet. Personal computer 26 may also include input devices such as a keyboard and mouse (not shown), a display monitor (not shown) and other peripherals such as a printer. The spectral domain interferometer system 20 is an optical device based on laser ranging technology. It uses a short coherence light source (broadband light source) to enable three-dimensional scanning of living tissue. In the illustrated embodiment, driver 24 includes a driving circuit 28 which powers a light source 30 in the form of a superluminescent diode (SLD) coupled with a fiber optic cable 32.

Fiber optic cable 32 extends from SLD 30 to its emitting end 36 and between driver housing 31 and probe housing 21. By using a first housing 31 for SLD 30 and its driving circuitry 28 and a second housing 21 for probe 22 with fiber optic cable 32 extending therebetween, the size of the probe housing 21 can be reduced thereby facilitating its use inside a conventional IVF operating chamber or other similar space with a controlled environment. It also allows housing 31 to house a mechanical fan 54 for cooling the drive circuitry 28 whereby probe housing 21 can be free of all mechanical cooling fans.

Communication and power cables 54 also extend from housing 31 to probe housing 21 to communicate electrical power and control signals to the probe 22 and communicate data in both directions. Similarly, communication and power cables 54 communicate electrical power and control signals from personal computer 26 to driver housing 31 and data in both directions.

The system allows for flexibility in the locating of the control circuitry. One or more control circuits are used to control the operation of drive circuitry 28 located in housing 31, detector 46, second image sensor 58 and servo motors 43 which are located in probe housing 21. For example, processor 27 located in personal computer 26 could be used to control the entire system 20. Alternatively, personal computer 26 could be omitted and control circuitry 29 located in the driver housing 31 could be used to control the entire system. Control circuitry 23 located in probe housing 21 may also be used. It will often be desirable for only limited control circuitry 23 to be located within probe housing and rely primarily on either control circuitry 29 and/or processor 27 for control of system 20 to thereby minimize the size and heat generation of the probe 22.

SLD 30 is a form of light emitting diode and provides a broadband light source with short coherence length that emits near infrared light. The near infrared light can penetrate relatively deeply into the three-dimensional COC with sufficient resolution for determining the maturity of the COC as further discussed below. The photon energy of the near infrared light emitted by SLD 30 is lower than visible light and much lower than ultraviolet (UV) light, therefore, it is safer than the use of both white light illumination which is widely used in IVF clinic practice and red LED illumination which has been recently adopted by IVF clinics. Compared to a traditional Ti-sapphire laser, SLD 30 is less expensive and more stable. Unlike laser diodes, the output intensity of an SLD does not exhibit a sharp threshold but instead gradually increases with the drive current. This characteristic facilitates its use at relatively low drive currents whereby the drive circuit can be set at a level that generates light at an intensity that is safe for fragile biological targets such as COCs.

Figure 2:
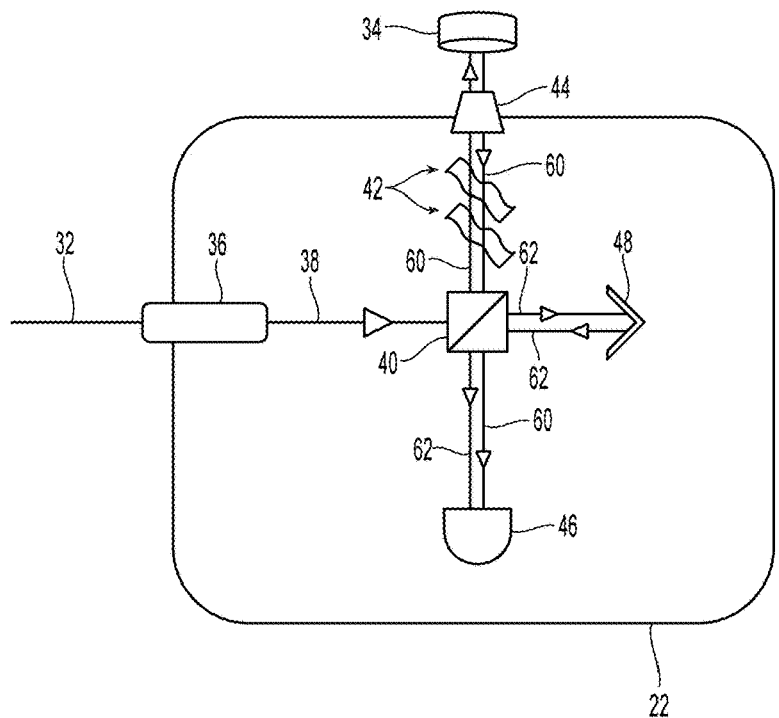
FIG. 2 is a schematic representation of a probe that can be used in a system for non-invasively assessing the maturity of an oocyte.

Interferometer 20 operates in spectral domain and probe 22 functions as a high-speed spectrometer. Probe 22 illuminates a biological sample 34 with a small focus and collects the back reflected and back scattered light from the focus volume to thereby form the signal light. With reference to FIG. 2, SLD 30 generates near infrared light that is transmitted through fiber optic cable 32 to the probe where it is emitted at emitting end 36. The emitted near infrared light 38 is projected at beam splitter 40. A portion of the light 38 entering beam splitter 40 is directed towards the biological target 36 through a scanning mechanism 42 and an objective lens 44. In the illustrated embodiment, scanning mechanism 42 is a pair of galvanometric scanning mirrors which are controllably rotated about a pair of mutually perpendicular axes. The back reflected and back scattered light passes back through the objective lens 44, scanning mechanism 42 and beam splitter 40 to detector 46 and forms the signal light 60. In the illustrated embodiment, detector 46 is a charge-coupled device in the form of a CCD image sensor.

Another portion of the light 38 entering beam splitter 40 is directed toward a reflecting prism 48 which then directs the light back to detector 46 through beam splitter 40 to form the reference light 62. Alternatively, a mirror or other reflector could be used to reflect the reference light directly back to detector 46 instead of through beam splitter 40. The signal light interferes with the reference light on the CCD screen 46 of the interferometer and thereby generates interferometric image data of the biological target.

Depth information of the interferometric image data can be reconstructed via Fast Fourier Transform (FFT) as is well known to those having ordinary skill in the art. The pair of galvanometric mirrors which are controllably rotated about mutually perpendicular axes provides a scanning mechanism 42 whereby the near infrared light can be controllably directed at different areas of the biological target 34. Two small servo motors 43 are used to rotate each of the galvanometric mirrors. The use of such galvanometric scanning mirrors is well-known to those having ordinary skill in the art. The combination of the depth information of each point of measurement and the use of the scanning mechanism to controllably direct the light at different areas of the biological sample, allows spectral domain interferometer system 20 to perform three-dimensional imaging of biological targets.

Figure 3:
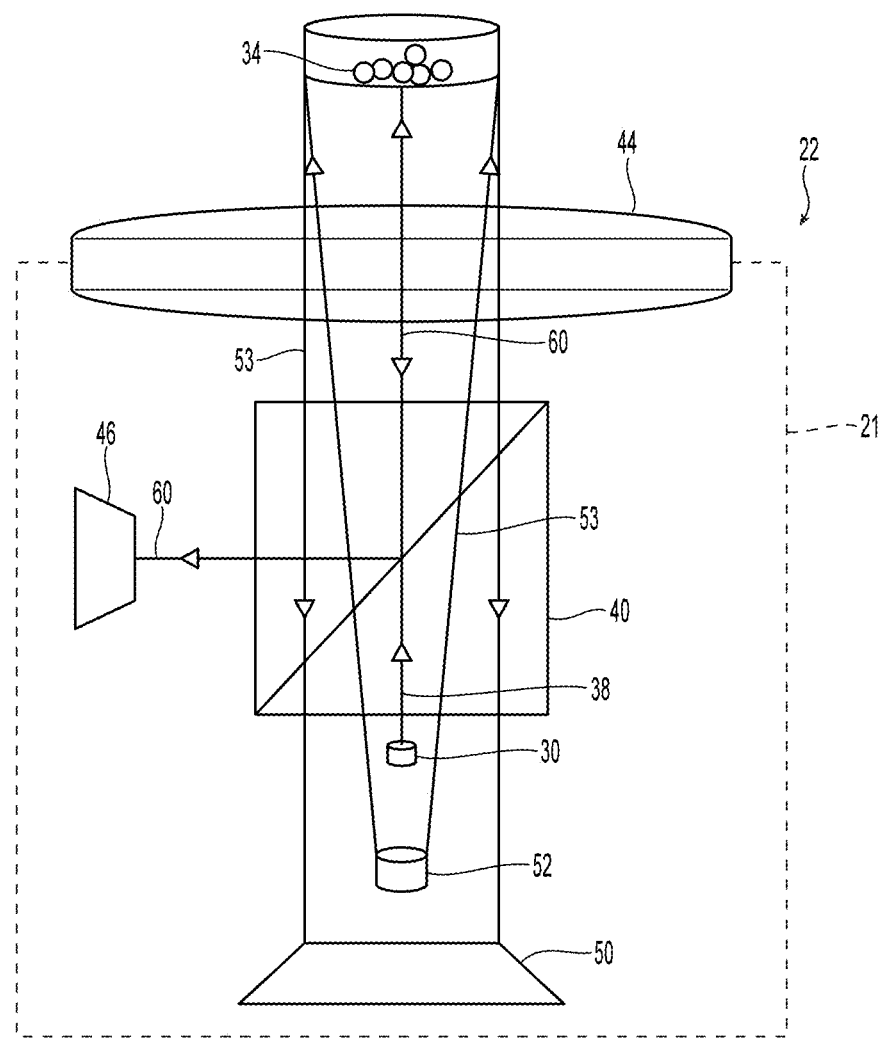
FIG. 3 is a schematic representation of another probe that can be used in a system for non-invasively assessing the maturity of an oocyte.

A second camera or image sensor 50 with a secondary light source 52 can be used in combination with probe 22 as schematically depicted in FIG. 3. Secondary light source 52 is chosen to avoid damage to the oocyte and avoid interference with the acquisition of interferometric data and may take the form of a white or red LED light. Camera/image sensor 50 includes a digital image sensor, such as a CCD sensor, and is used to provide a real time two-dimensional image. Image sensor 50 and light source 52 can be mounted within, attached or fixed relative to probe 22 to facilitate focusing on the desired target and performance of the 3D scan with probe 22. The use of image sensor 50 and a white or red LED light 52 should not impair the spectral domain scan performed with probe 22. Light 53 generated by light source 52 is captured by image sensor 50 to obtain a two-dimensional image of the biological target.

In FIG. 3 the light generated by LED 52 and collected by image sensor 50 reaches the biological target 34 and returns to sensor 50 via beam splitter 40 and objective lens 44. In this regard, it is noted that the coating used with beam splitter 40 may be selected such that it reflects most of the near infrared light 38 generated by SLD 30 while allowing most of the white/red light 53 generated by LED 52 to pass therethrough.

Additional or alternatively positioned white light image sensors may also be employed with system 20. For example, image sensor 50 may also be used to obtain an image of the sample holder 64 in which the biological target is held. Sample holder 64 may take the form of a transparent petri dish. An identifying label 66, such as simple text, a bar code, a matrix bar code such as a QR code, an RFID tag or other identifying material can be affixed to or formed on sample holder 64 and image sensor 50 or other image sensor coupled with system 20 can be used to acquire a two-dimensional image of the identifying label 66. The image of the identifying label can be associated with the interferometric data acquired by system 20 of the biological target 34 within the sample holder 64. Alternatively, the identifying information can be input through another input device associated with system 20. For example, a keyboard associated with personal computer 26 could be used to input the identifying information. This allows for greater efficiency in the processing of multiple sample holders and the assessment of the biological targets located therein. For example, one person can focus on imaging the biological targets without stopping to analyze the results after acquiring images of each sample while the assessment of the images takes place on a parallel track as further discussed below.

Figure 4:
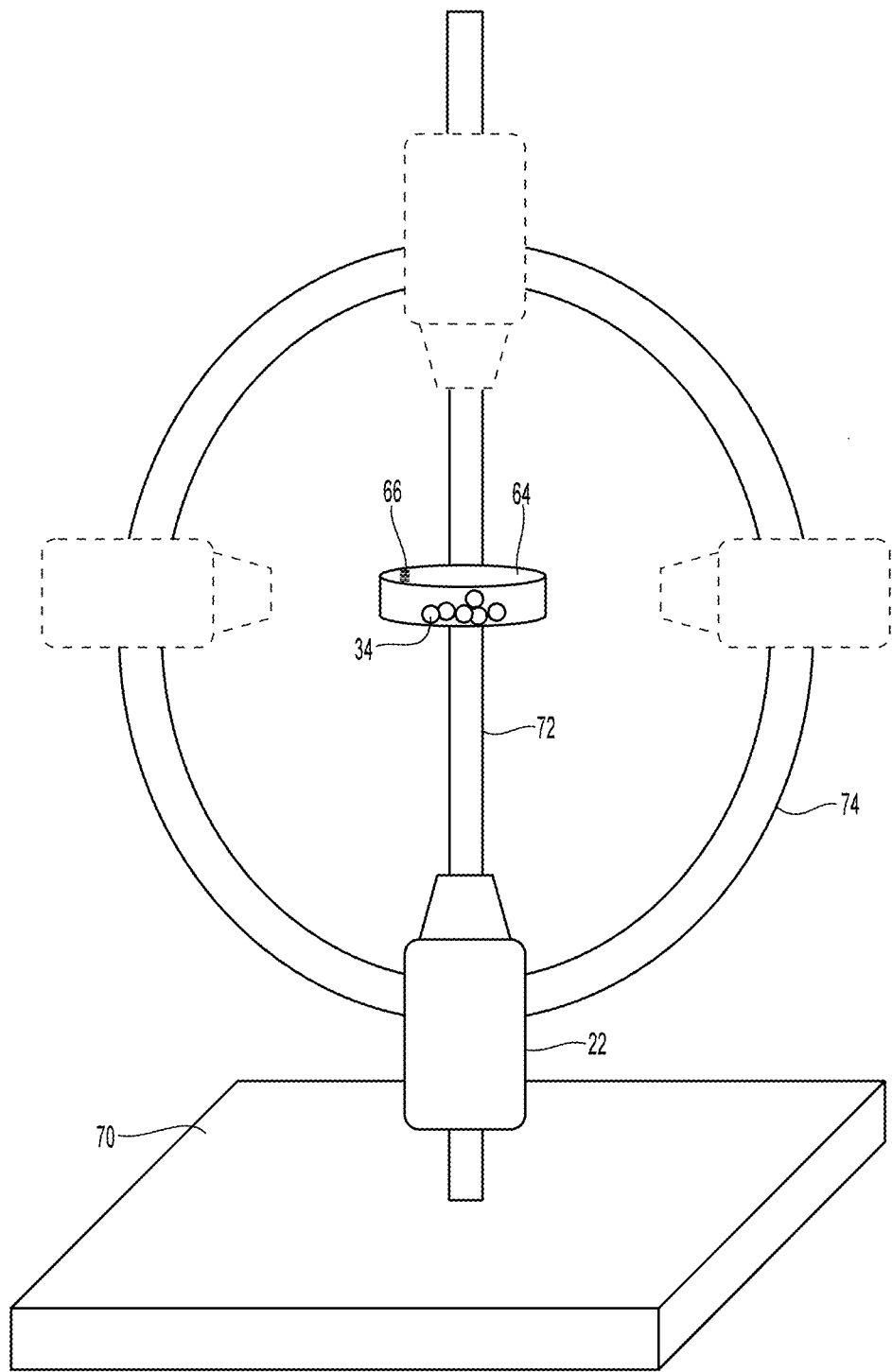
FIG. 4 is a schematic representation of a support structure supporting a probe and biological target.

FIG. 4 depicts a sample holder 64 with an identifying label 66 positioned on the target support ready for imaging. In practice, an imaging sample holder 64 which does not include a label may alternatively be used. For example, the oocytes/COCs may be stored in storage sample holders 64 which have identifying labels 66 with the oocytes/COCs being temporarily removed from their storage sample holders 64 and placed in the imaging sample holder for imaging. After completing the imaging, the oocytes/COCs are returned to the same storage sample holder 64 from which they were removed.

In IVF clinics, when using a microscope or other traditional optical method to observe COCs/oocytes, the objective lens can be positioned either above or below the sample depending on the optical method preferred by the clinic. For example, if the clinic uses an inverted microscope, the objective lens will be below the sample and if an upright microscope is used the objective lens will be above the sample. Either way, there is only transparent liquid (growth medium and oil) between the objective lens and the targets so that it is easy to get a relatively clear 2D microscopic image.

Figure 5:
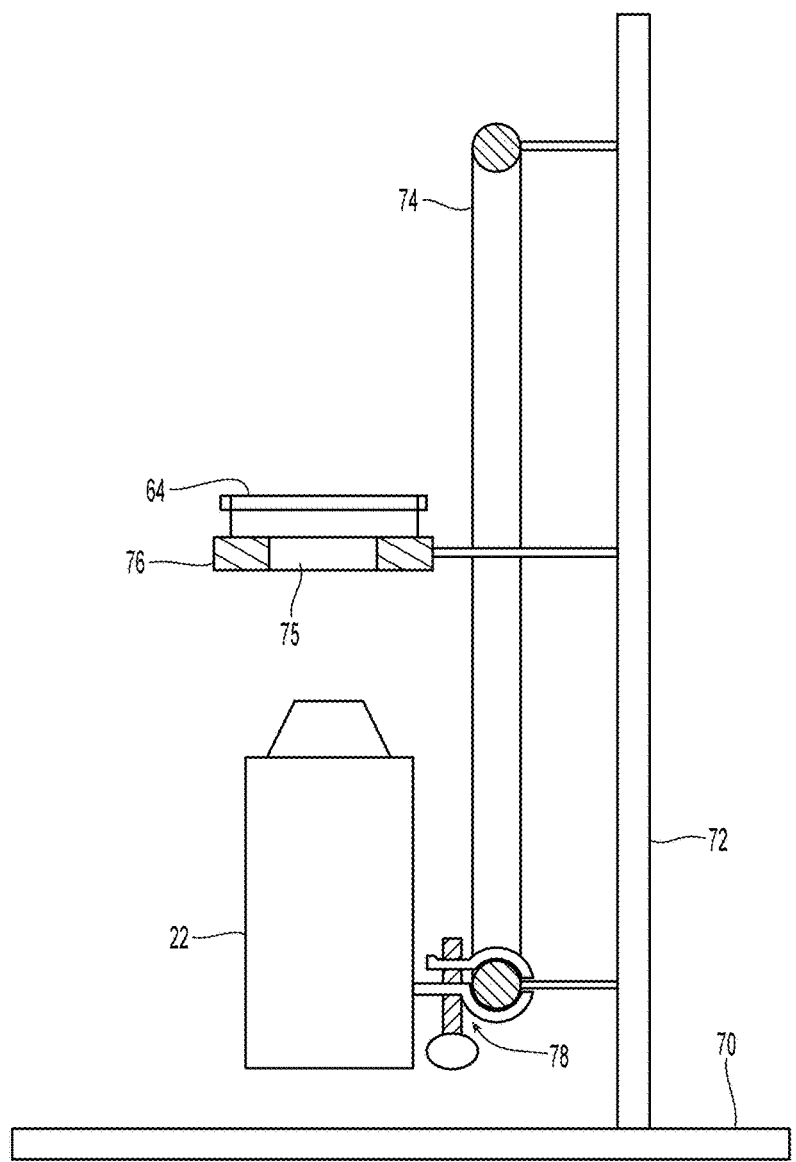
FIG. 5 is a side view of the support structure of FIG. 4.

The relatively small size of probe 22 allows it to be used to obtain data from the biological target at various angles. Support structure 68, shown in FIGS. 4 and 5, provides a framework for supporting probe 22 at many such different angles. Support structure 68 includes a base 70 which rests on a horizontal surface and has an upright 72 extending vertically therefrom. A support ring 74 is attached to upright 72 and probe 22 is selectively securable to the support ring 74 using a clamping mechanism 78. Various other mechanisms may also be used to secure a probe to a support ring or other support structure such as threaded fasteners or the use of openings on the support structure into which a projection is inserted. The probe may also allow such different attachment mechanisms to be interchanged. For example, the probe housing may have a socket into which a shaft of the attachment mechanism is removably inserted, or, a threaded bore into which the shaft of an attachment mechanism is removably secured.

A target support 76 is secured to upright 72 near the center of support ring 74 whereby a probe 22 attached to support ring 74 can be positioned to view a biological target positioned on the target support 76. For example, a sample holder 64 in the form of a petri dish with a biological target disposed therein can be positioned on target support 76. In this regard, it is noted that target support 76 has a generally toroidal shape with a central opening 75 which is smaller than the diameter of the petri dish but still sufficiently large whereby the probe can direct signal light at the biological target through the central opening from below the target support. Alternatively, the center of the target support 76, or a larger portion of the target support, could be formed out of a transparent material, similar to that of the sample holder 64, that would allow the passage of visible light and near infrared light without significant interference. Target support 76 may also include a heating element, such as an electrical resistance heater, to ensure that the biological target remains within a desired temperature range.

Probe housing 21 is securable to support ring 74 at different locations encircling the target support 76 as depicted in FIG. 4 which illustrates four potential locations where probe 22 can be attached to support ring 74 whereby the probe can direct signal light at the biological target from the bottom, top or two opposite sides. This allows probe 22 to direct signal light at the biological target from a plurality of different positions and thereby collect interferometric image data from a variety of different angles.

It will oftentimes be most advantageous for probe 22 to illuminate and observe the target from below instead of above as is typical with a conventional microscope. One advantage of positioning probe 22 below the biological target 34 is that the embryologists maintaining the oocytes and performing the assessment do not need to control the depth of growth medium and oil as precisely in order to get a clear focused image as when observing the biological target from above when the depth of such materials can have a significant impact on the observation.

Another advantage provided by the use of probes 22 and support structure 68 is that it allows for the simultaneous use of multiple probes 22 as can be clearly understood with reference to FIG. 4. When imaging extremely large COCs which are more than 1 mm in diameter, it will generally be advantageous for two probes 22 to be attached to support structure 68 to image the COC from two opposing sides to obtain a full 3D image of the COC.

Figure 8:
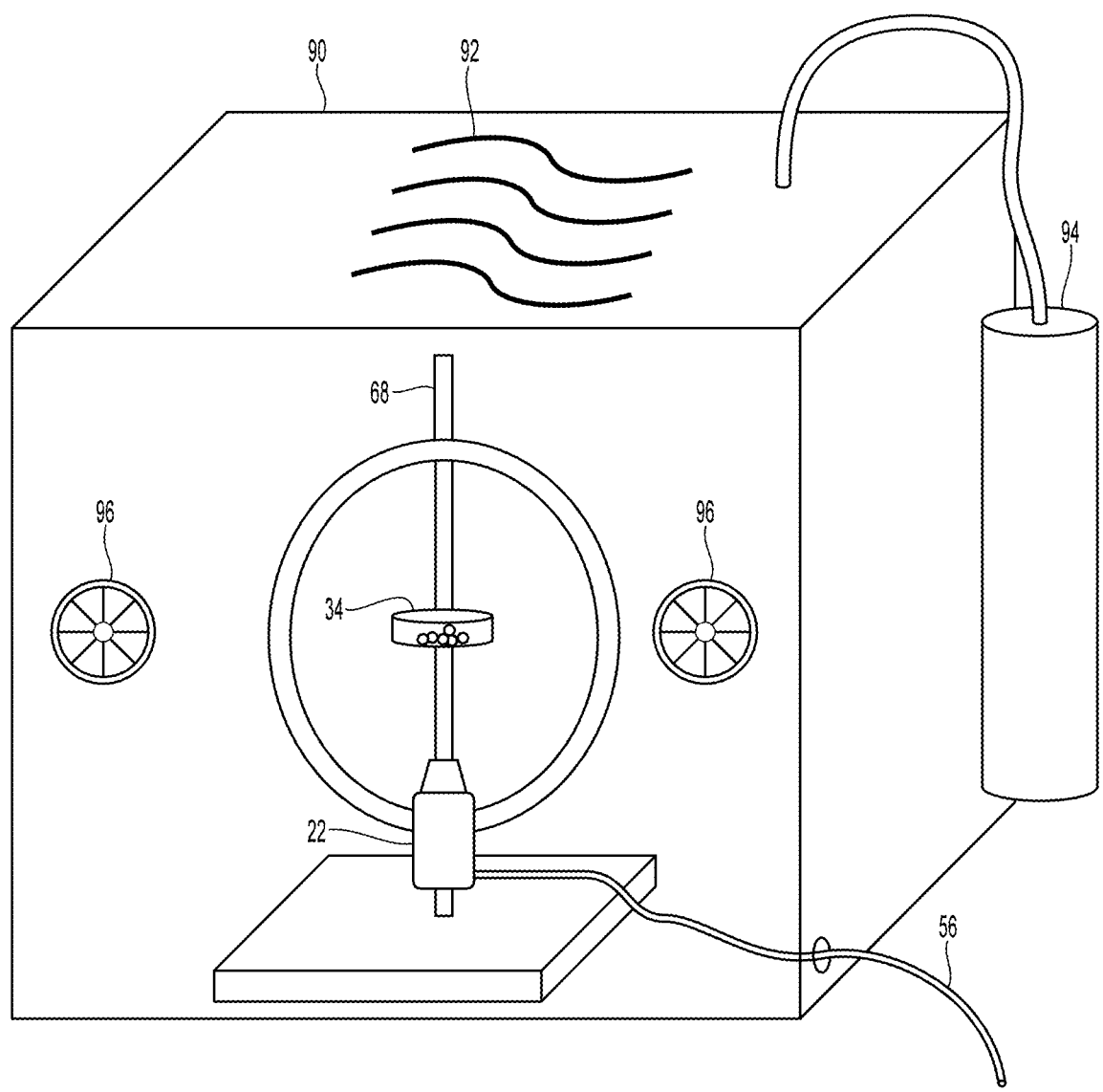
FIG. 8 is a schematic view of a probe mounted on a support structure within an IVF operating chamber.

FIG. 8 schematically depicts a probe 22 secured to a support structure 68 positioned inside a controlled environment chamber 90. The use of such controlled environment chambers is common when working with oocytes. Chamber 90 includes heating elements 92 which are used to control the temperature within chamber 90 and a $CO_2$ gas supply 94 which is used to ensure the proper mix of gas within chamber 90. Access portals 96 allow a person to insert their hands into the chamber to manipulate the contents.

Figure 6:
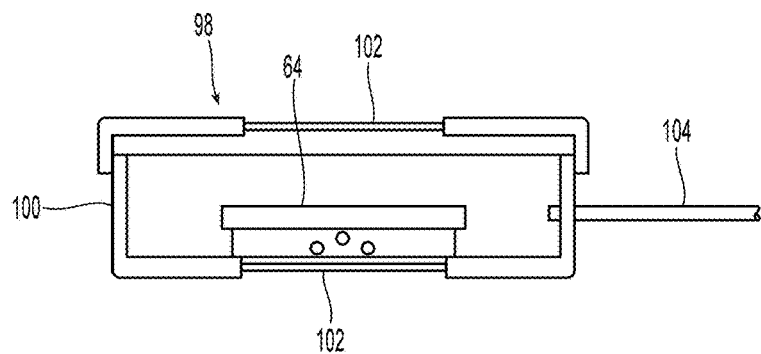
FIG. 6 is a schematic view of a target support which fully encloses a sample holder.

FIG. 6 depicts an alternative controlled environment chamber 98 that can be used with probe 22. Chamber 98 is a small chamber designed to provide a controlled environment for sample holder 64 and be positioned on target support 76 for imaging by a probe 22. Chamber 98 includes a housing 100 with a removable cap. Transparent windows 102 located on the top and bottom surfaces of chamber 98 allow imaging of the biological target held within chamber 98. Alternatively, the entirety of housing 100 could be formed out of transparent materials which allow the passage of visible light and do not interfere with the acquisition of interferometric data. A tube 104 is used to supply $CO_2$ gas to the chamber. A heating element could also be incorporated in housing 100, housing 100 could be positioned on top of a thermally controlled surface, or the temperature of the $CO_2$ gas entering the chamber could be controlled to thereby control the temperature within chamber 98.

Figure 7:
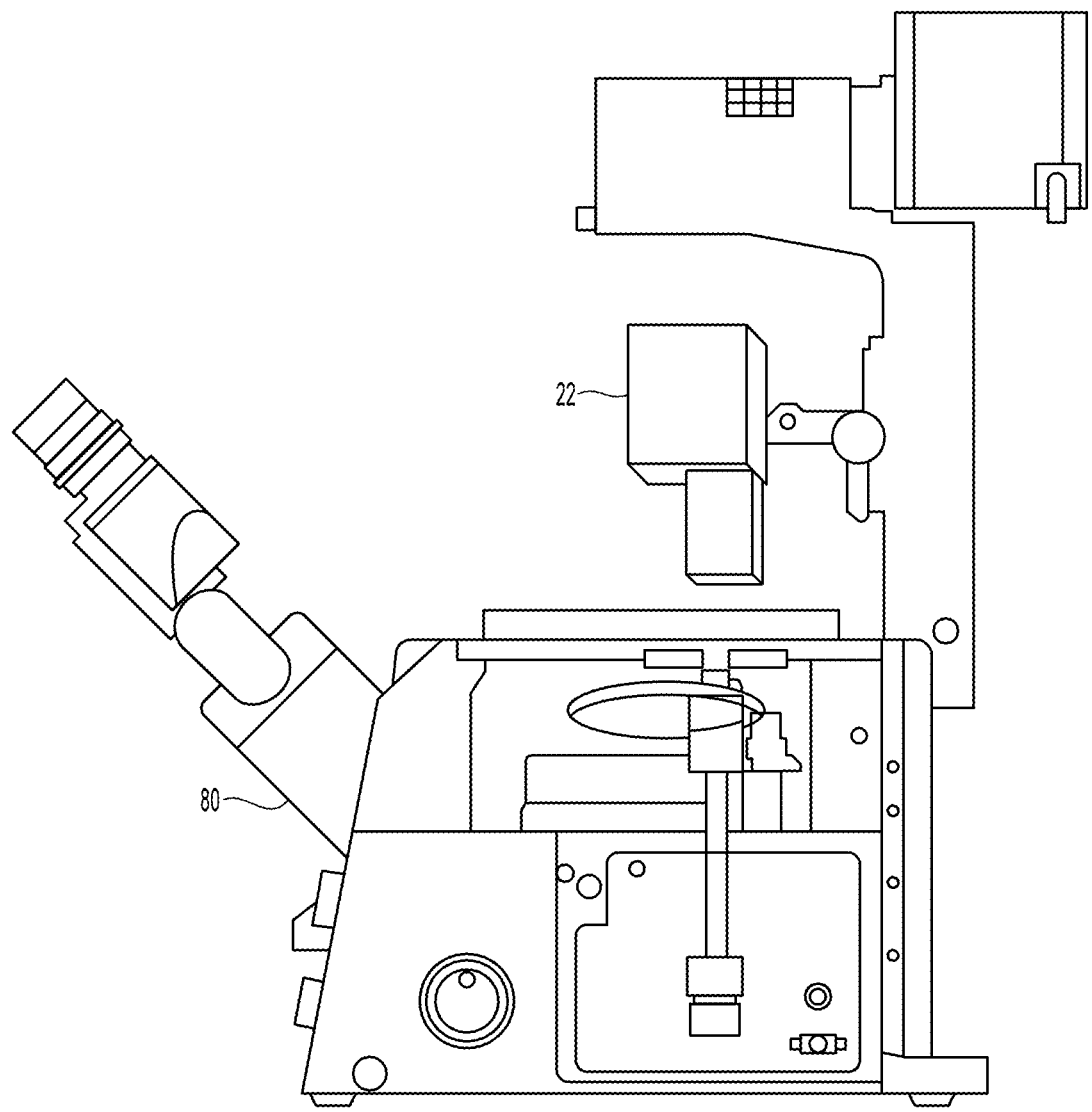
FIG. 7 is a schematic view of a probe mounted on a microscope.

FIG. 7 illustrates how probe 22 can be used with a conventional microscope.

Microscope 80 depicted in FIG. 7 is an inverted microscope having a probe 22 attached at a location where it can be used to observe the specimen being viewed with the microscope. Many IVF clinics have controlled environment chambers with conventional microscopes mounted therein so that a specimen can be viewed with the microscope with the specimen inside of the controlled environment chamber. Probe 22 can be readily adapted for use with such existing equipment by attaching the probe 22 to the microscope in a position where it can be used to image the biological target being viewed with the microscope.

Turning now to the assessment of the maturity of an oocyte with probe 22, it is noted that the determination of oocyte maturity relies on the observation of the first polar body. The appearance of the first polar body is the sign of maturity of an oocyte/COC. In a COC, however, it cannot be seen using a conventional microscope because the layer of cumulus cells is too thick. Imaging with probe 22 does penetrate the COC and does allow for a 3D image of the COC to be generated. Such imaging can be done quickly and at relatively high resolutions. For example, probe 22 may enable such imaging to be completed within 10 seconds and at a resolution of 5 micrometers in three mutually perpendicular directions.

Figure 9:
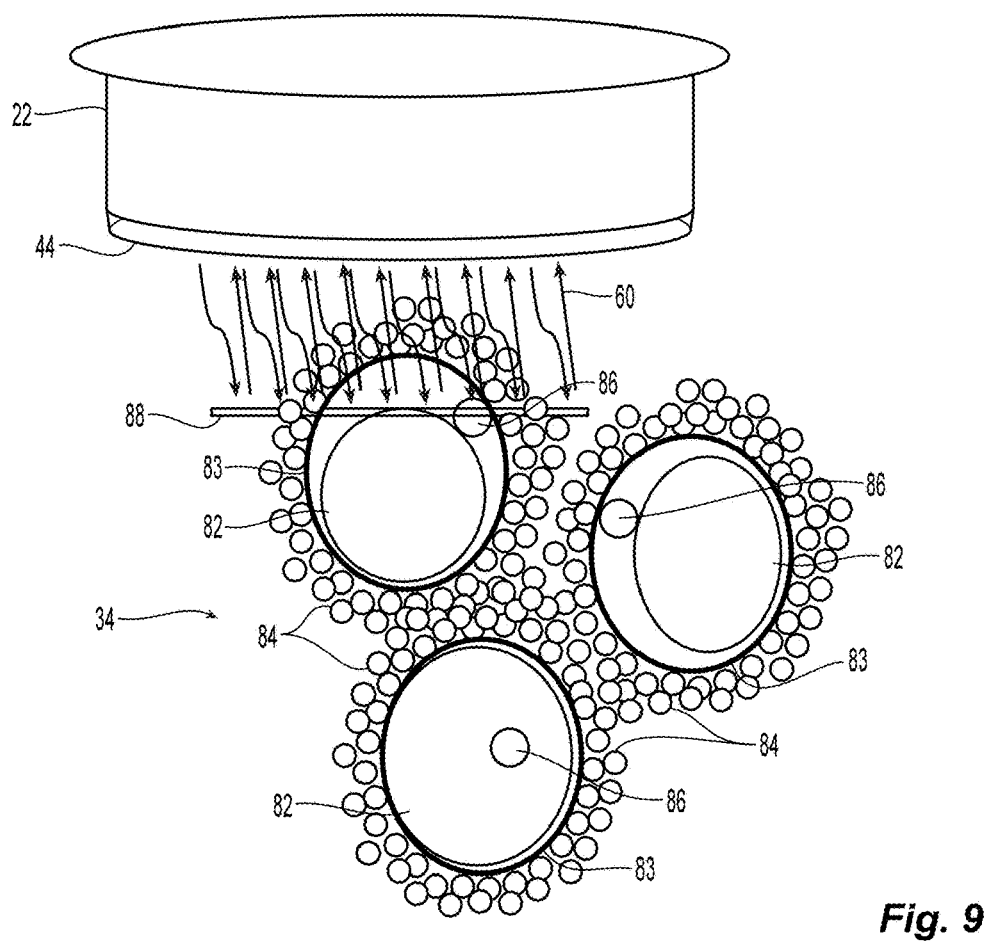
FIG. 9 is schematic view of a portion of a probe and a biological target.
Figure 10:
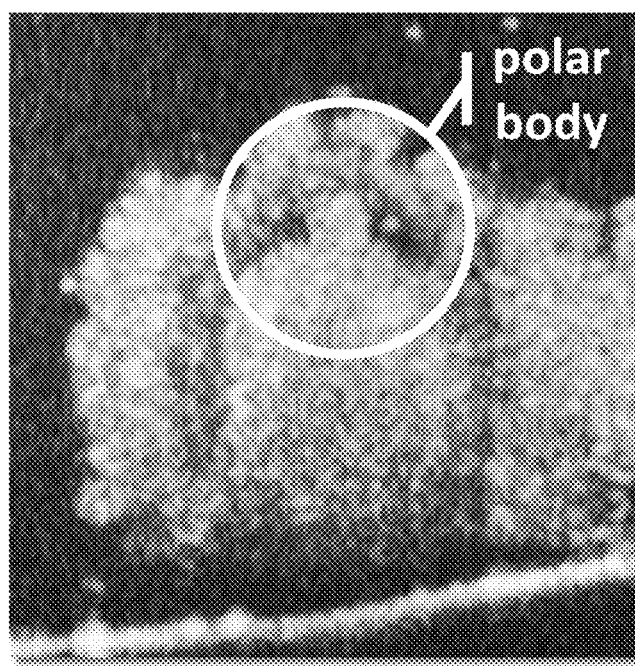
FIG. 10 is an interferogram of a biological target.

FIG. 9 schematically depicts the acquisition of interferometric data of a COC with probe 22 while FIG. 10 is an image generated from interferometric data acquired with a probe 22 which may also be referred to as an interferogram. FIG. 9 has been drawn to correspond to a situation that could result in the generation of an image such as that depicted in FIG. 10. In FIG. 9, a cumulus-oocyte-complex (COC) having three oocytes 82 surrounded by cumulus cells 84 is depicted. The oocytes 82 depicted in FIG. 9 are mature oocytes and each have a polar body 86 located within the oocyte's zona pellucida 83 (shell). Probe 22 is projecting signal light onto one of the oocytes and collecting the reflected and backscattered signal light 60. In this schematic depiction, the probe is imaging the oocyte to a depth that extends to imaging plane 88 and thereby captures a polar body within the region of interest. A polar body in the interferogram of FIG. 10 is circled.

By providing the ability to assess the maturity of an oocyte within a COC without denuding the cumulus cells, system 20 provides a significant advantage over conventional assessment techniques used in IVF which require the denuding of the COC to assess the maturity of the oocyte. With system 20, denuding the COC is not required and if it is determined that the oocyte within the COC is immature, the oocyte can be allowed to continue to develop. If the oocyte is denuded before determining that the oocyte is immature, it generally must be discarded because without the cumulus cells it will generally be unable to mature.

The use of adjustable galvanometric mirrors 42 allows location of the region of interest to be adjusted. Adjustable mirrors may also be used in the path of the reference light to adjust the length of the reference light path to thereby selectively adjust the depth of the interferometric data. Alternatively, the reference light path length could be fixed and the position of the probe or the use of multiple probes could be employed if the fixed depth of the scan was not sufficient for obtaining the desired interferometric data. In other words, the biological target or probe could be physically moved to adjust the region of interest and/or, as discussed above, multiple probes 22 may be used simultaneously to provide greater coverage.

Probe 22 has been used to test numerous COCs from different species such as porcine, murine, and buffalo. It has demonstrated an accuracy of 92% when distinguishing matured and immature COCs. A probe 22 has also been used to image a human cumulus cell layer and it was able to penetrate the layer and obtain a clear image. FIGS. 11A-11E are examples of matured and immature porcine and murine COCs.

Figure 11A:
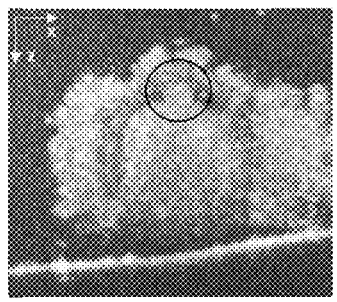
FIG. 11A is an interferogram of a COC with a polar body.
Figure 11B:
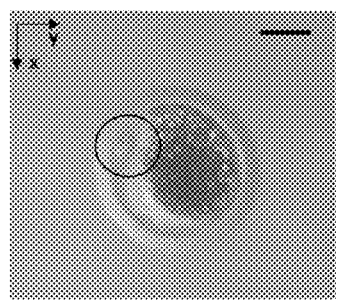
FIG. 11B is a microscopic image of an oocyte with a polar body.

FIGS. 11A-D are images of porcine samples. They were harvested when immature and then subjected to an in vitro maturation (IVM) process. FIG. 11A is an interferogram of a matured COC and the first polar body circled. FIG. 11B is a microscopic image of the oocyte of FIG. 11A after the COC was denuded. The microscopic image confirms the presence of the polar body and the accuracy of the assessment obtained by the use of probe 22. Please note that FIG. 11A is a view from the y direction, it is a vertical cross section of the COC. FIG. 11B is a view from z direction, it represents a horizontal (xy) plane.

Figure 11E:
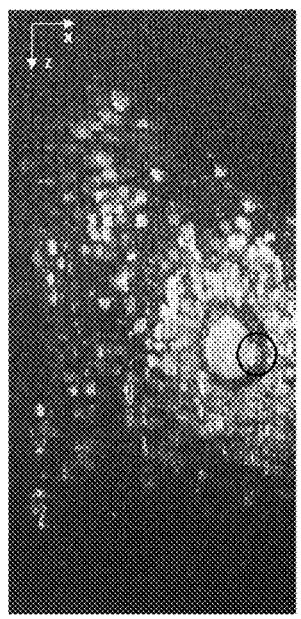
FIG. 11E is an interferogram of a COC with a polar body.
Figure 11C:
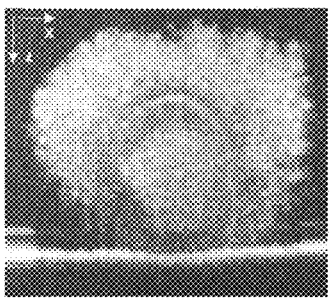
FIG. 11C is an interferogram of an immature COC.
Figure 11D:
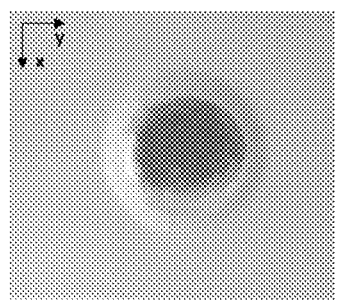
FIG. 11D is a microscopic image of an immature oocyte.

FIGS. 11C and 11D are a similar pair of images of an immature COC. FIG. 11C is an interferogram of the immature COC and FIG. 11D is a microscopic image of the immature oocyte of FIG. 11C after it has been denuded to confirm the accuracy of the assessment made using the interferogram.

FIG. 11E is an interferogram of a murine COC providing a vertical cross sectional view. The COC was a part of a naturally matured COC cluster harvested from a wild-type mouse. The oocyte is smaller while the COC as a whole is much looser and larger.

Figure 12A:
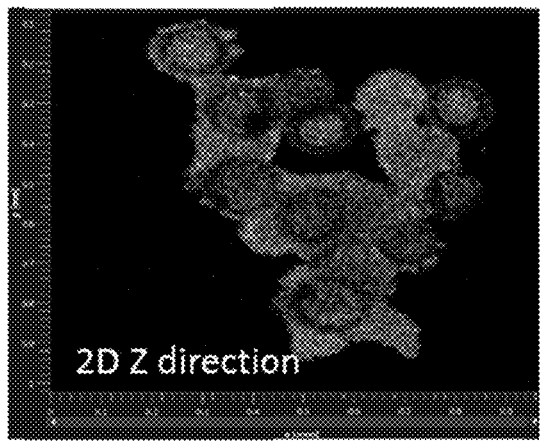
FIG. 12A is an interferogram of a multi-oocyte porcine COC.
Figure 12B:
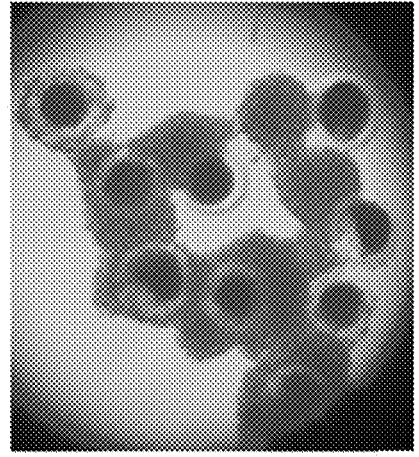
FIG. 12B is a microscopic image a multi-oocyte porcine COC.
Figure 12C:
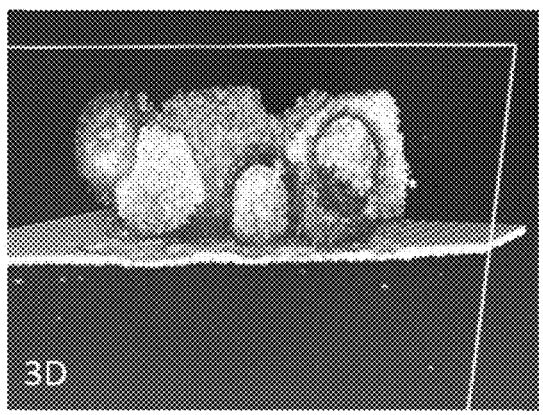
FIG. 12C is an interferogram of multi-oocyte porcine COC taken from a different perspective than that of FIG. 12A.
Figure 12D:
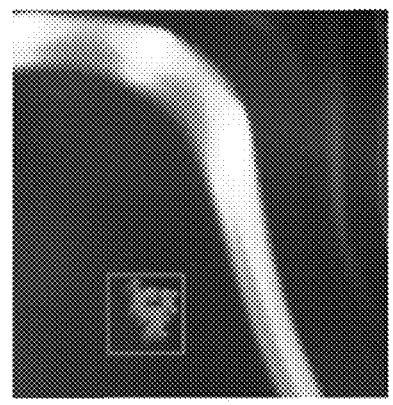
FIG. 12D is an image acquired with a second image sensor of a multi-oocyte porcine COC.

FIG. 12A shows a two-dimensional image reconstructed from the interferometric image data of a multi-oocyte porcine COC. FIG. 12B is a microscopy image that has been enlarged 5 times of a multi-oocyte porcine COC. FIG. 12C is a three-dimensional image reconstructed from the interferometric image data of a multi-oocyte porcine COC. FIG. 12D is a non-magnified two dimensional image obtained with an image sensor from reflected white light of a multi-oocyte porcine COC.

Figure 13B:
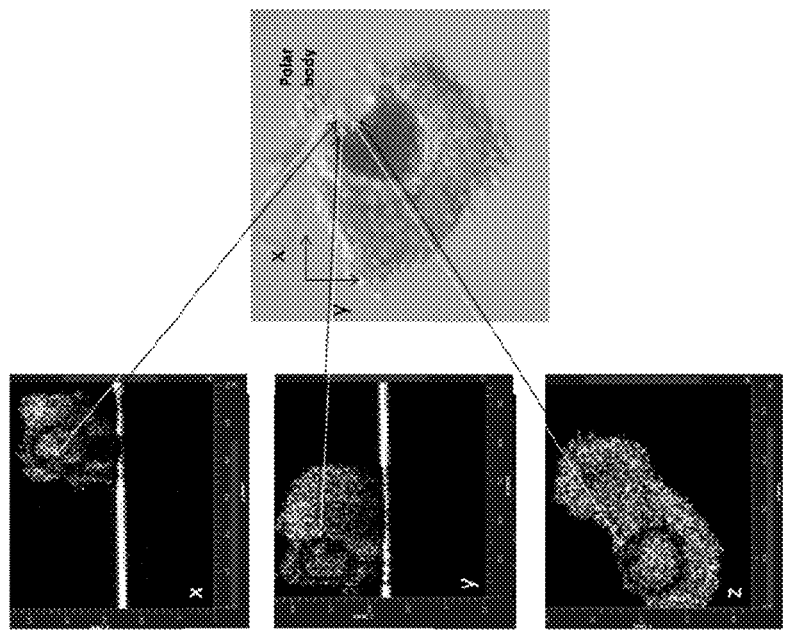
FIG. 13B shows a microscopic image of the COC of FIG. 13A after it has been partially denuded and three interferograms of the same COC.
Figure 13A:
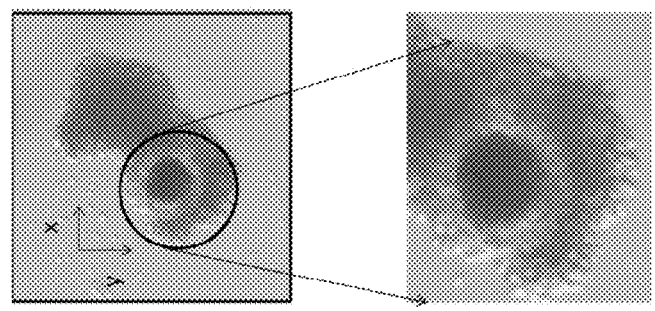
FIG. 13A shows two microscopic images of a COC.

FIG. 13A is a microscopy image of a COC with an enlarged portion of the porcine COC. FIG. 13B contains images of the same porcine COC with three interferograms showing cross sections at three mutually perpendicular angles wherein the interferograms show a polar body. A microscopy image of the same COC after it has been partially denuded of its cumulus cells to reveal the polar body confirms the ability to make an accurate assessment of the COC with the interferograms.

Figure 14:
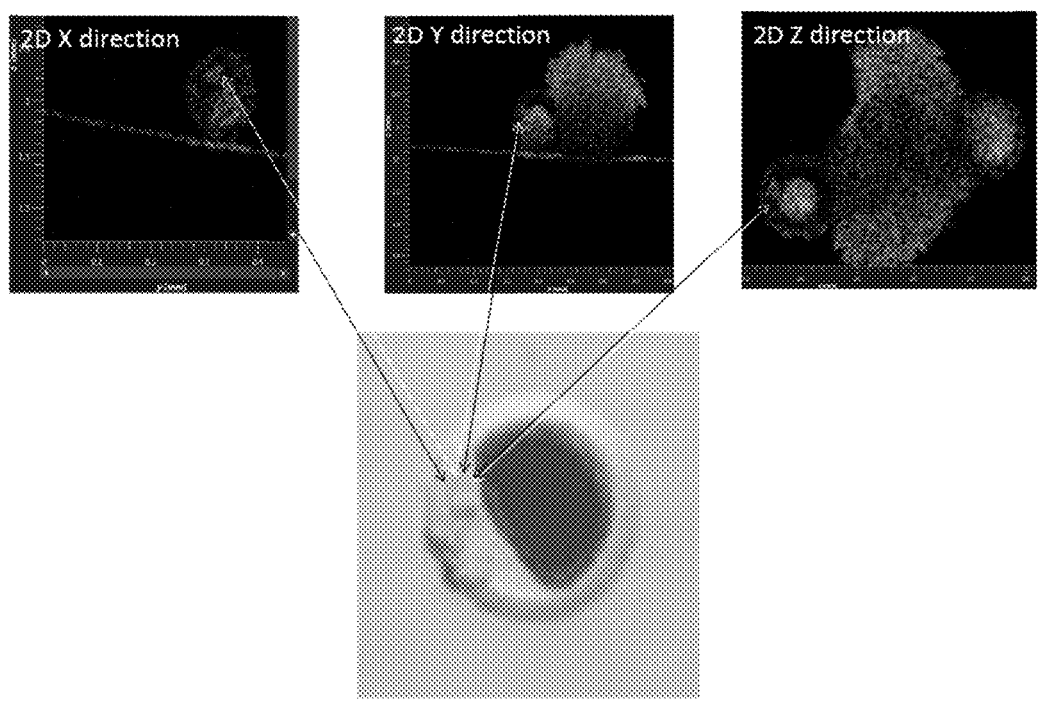
FIG. 14 shows three interferograms of a COC showing a polar body and a microscopic image of the denuded COC confirming the presence of the polar body.

FIG. 14 provides three interferograms of a porcine COC showing cross sections at three mutually perpendicular angles wherein a polar body is visible and a microscopy image of the same COC after it has been fully denuded.

Figure 15:
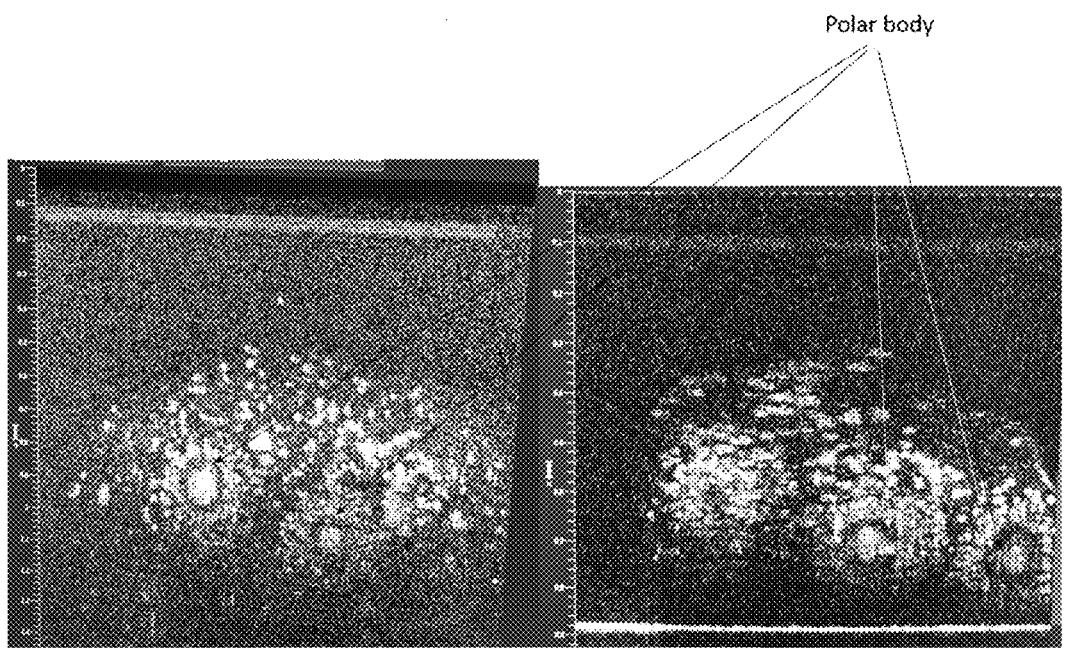
FIG. 15 shows two interferograms of murine COC clusters.

FIG. 15 provides two interferograms of murine COC clusters identifying several polar bodies therein.

The use of near infrared light allows probe 22 to assess a COC without damaging the COC. Advantageously, the near infrared light generated by the light source has a wavelength within the range of 800 micrometers to 1000 micrometers. In the illustrated embodiment, SLD 30 generates near infrared light having a wavelength of 850 micrometers. The intensity and duration of the light used with the biological target and the resulting light energy to which the biological sample is subjected is also a factor in preventing damage to the biological sample due to the assessment process. Advantageously, the near infrared light generated by the light source has a power of no more than 5 milliwatts and the step of projecting the signal light portion of the near infrared light onto the biological target exposes an individual oocyte to no more than 100 millijoules of energy from the near infrared light. Limiting the exposure of the biological targets to light which does not exceed these limits should maintain the viability of the oocytes. Other types of biological targets could be subjected to more intense light and greater light energy without damage. For example, a typical cancer tissue could tolerate 30 milliwatt light for hours.

Conventional 3D imaging techniques like confocal microscopy, two-photon microscopy and light sheet microscopy can generate a 3D image of a COC. However, the light intensity of these techniques is too high for maintaining the viability of the COCs. After conducting imaging with such conventional techniques, the COCs are permanently damaged. These conventional techniques can be useful in scientific labs to study the COCs, but they are not useful in an IVF clinic where maintaining the viability of the COC is essential.

The photon energy of the near infrared light generated by SLD 30 is much lower than blue and UV light due to the nature of the light. The near infrared photon is much less likely to damage the oocyte DNA. Also, because the power of SLD 30 is low (less than 5 milliwatts) and the very short imaging time (for example, less than 10 seconds per COC), the total energy to which the COC is exposed during the imaging process is comparable to the energy exposure of a COC in a typical IVF clinic environment using conventional microscopy.

A light safety was completed using a probe 22 on murine COCs to confirm the photon safety of the probe 22. In this study, ten to fifteen wild-type female mice were prepared for the test. On Day 1, the female mice were injected interperitoneally (IP) with pregnant mare serum (PMS). The females were housed five or fewer per cage. On Day 3, forty-two to fifty hours after the PMS injection, the mice received an IP injection of human chorionic gonadotropin (HCG). Ovulation occurs approximately 12 hours after the HCG injection. On Day 4, for each mouse, COC clusters were harvested from both ovaries and were randomly placed to two groups: a test group and a control group.

A probe 22 was used to perform imaging of the COC clusters in the test group and thereby subjecting them to near infrared light generated by probe 22 during the imaging. The COC clusters were subjected to near infrared light for approximately 30 seconds. The COC clusters in the control group were not subjected to light exposure but were otherwise subjected to the same conditions as the test group. After the light exposure of the test group, each group was combined with sperm and went through a normal mouse IVF procedure. On Day 5, the biologists counted the 2-cell development in both groups. This testing was done at two facilities and the results are shown in the following table:

|  | Facility 1 | | | Facility 2 | | | Total | | |
| --- | --- | --- | --- | --- | --- | --- | --- | --- | --- |
|  | 2-cell | COC | 2-cell Ratio | 2-cell | COC | 2-cell Ratio | 2-cell | COC | 2-cell Ratio |
| Ctrl Group | 56 | 129 | 43.4% | 74 | 212 | 34.9% | 130 | 341 | 38.1% |
| Test Group | 43 | 110 | 39.1% | 80 | 221 | 36.2% | 123 | 331 | 37.2% |

Approximately 240 COCs were in the two groups at one facility and about 430 COCs were in the two groups at the other facility. The number of COCs in the test and the control group were equally distributed. For one facility, the control group had a slightly better 2-cell rate; for the other facility, the test group had a slightly better 2-cell rate. For all of 672 COCs that were tested in the two facilities, the test group 2-cell ratio was 37.2%, and the control group 2-cell ratio was 38.1%. This difference is not statistically significant.

Based upon these results, the near-infra red light used by probe 22 is considered safe for the development of murine COCs.

Efficacy of system 20 was tested and affirmed by assessing interferometry images of 147 fresh porcine oocytes as either mature or immature. Then, they were denuded and blindly re-scored by an experienced embryologist using conventional microscopy. Maturity of the oocytes was correctly assessed with the interferometric data in 135 (91.8%) of the 147 porcine COCs that were evaluated. Seven of the assessments (4.8%) were falsely-negative and five (3.4%) were falsely-positive (sensitivity=89.7%, specificity=93.7%).

Probe 22 is well-suited for use in an IVF clinic due to several aspects of probe 22 discussed above. More specifically, the use of a near-infra red light provides imaging safety for the COC/oocyte. Near infra-red light also provides good penetration depth and lateral resolution and can be deployed at an intensity and duration that is safe for the COC/oocyte.

The time it takes to capture a 3D image with probe 22 is very short. It is possible to acquire a full 3D image of a COC in less than 10 seconds. Thus, the process would not add significant time to current IVF clinic practice.

The use of support structure 68 also facilitates the use of probe 22 in an IVF clinic. This set up allows COC imaging from multiple different angles and also allows large COC's to be simultaneously imaged by multiple probes 22. When using multiple probes, the total imaging time will be substantially the same as using a single probe because the probes can collect data simultaneously. A small controlled environment chamber 98 may also be used with probe 22 if space is tight.

The modular design of system 20 as depicted in FIG. 1 is also well-suited for use in a typical IVF clinic. As schematically depicted in FIG. 1, the system may include a probe 22 which is connected by cable 56 to a driver 24 which, in turn, is connected to a personal computer 26. These three main components are separate from each other connected only by cables that transmit digital signals (for data and control), electrical power or light (via fiber optic cable 32).

This modular design provides several advantages. First, it allows probe 22 to be relatively small in size and thereby fit within a conventional controlled environment chamber which are found in many IVF clinics. For example, probe 22 can have a size that is approximately 15 cm in length and is no larger than approximately 8.5 cm in any direction perpendicular to the length axis. The driver 24 and personal computer 26 can be located outside the chamber and connected to the probe 22 by a cable 56.

The use of a separate housing for the probe and the other components of the system reduce the vibrations which can degrade image quality. For example, mechanical cooling fans 54 can be used with driver 24 and personal computer 26 while probe 22 can be free of such mechanical cooling devices to thereby isolate the probe from the vibration caused by such fans.

The modular design is also easily expanded. For example, multiple drivers 24 and probes 26 can easily be used to simultaneously image a single biological target and can also be attached to a single personal computer.

System 20 can be used in a variety of different ways. For example, it can be used in a relatively large controlled environment chamber 90 as can be seen in FIG. 8 which are often found in IVF clinics. When used in a chamber 90, the probe may be attached to a conventional microscope as depicted in FIG. 7. When used with a conventional microscope, the probe 22 can be attached at a location on the microscope such that when the targeted COC appears in the microscopy ROI (region of interest) it will also be in the ROI of the probe 22. The probe 22 can be used by itself with a support structure 68 inside of a chamber 90 to provide a more open operational environment within the chamber. The probe can also be used outside of a chamber 90, for example with a support structure 68 or attached to a microscope. When used outside of a chamber 90, the biological target may be taken out of a controlled environment, imaged and then quickly returned to the controlled environment. Alternatively, the biological target may be placed in a small controlled environment chamber 98 such that the speed at which the biological target is returned to its storage location in a controlled environment is not as critical. These different manners in which probe 22 can be used provide clinics with flexibility in determining how to integrate the use of such a probe into their practice.

It is envisioned that imaging software will allow for one click operation of the probe. Probe 22 can be configured such that it is a special purpose probe designed to work specifically with COC/oocytes rather than a general purpose that must have numerous parameters set to account for different applications such as light wavelength, intensity and depth of scan. As a result, once the COC is in the ROI of the probe, the embryologist can simply actuate the recording of interferometric image data with a single mouse click or other simple actuating method. The software will then collect and reconstruct the 3D image of the COC.

The process of assessing COC/oocytes for maturity can be semi-automated by using an image analysis algorithm. Because a large number of COC image data will be collected, a machine-learning based algorithm can be used with the images. The algorithm should be able to quickly analyze newly acquired 3D COC images and identify the possible image of a polar body within the COC. This provides initial maturity check suggestion to the embryologist, who can then view and analyze the area highlighted by the algorithm. This will save the embryologist valuable time when reviewing each 3D COC image when performing a maturity check.

The acquisition and analysis of the images may also be performed simultaneously by two or more different people. For example, the 3D images of COCs acquired with probe 22 can be uploaded to a local network or remote digital storage location (i.e., cloud storage). A second embryologist can then review the images to assess the maturity of the oocytes/COCs as the first embryologist continues to perform the imaging.

A COC identification system is advantageously employed with system 20. In a conventional IVF clinic, the embryologists individually handle and immediately classify oocytes and do not need to individually identify and distinguish between oocytes/COCs. When using a probe 22, it may be most efficient to separate the steps of imaging the oocytes/COCs and performing an assessment based upon those images. As a result, it will be advantageous to provide each oocyte/COC with an identifying label 66 so that the imaging results for each oocyte/COC can be matched with the proper oocyte/COC.

For example, identifying labels 66 can take the form of unique barcodes for each oocyte/COC. Image sensor 50 or other image sensor or input device in communication with system 20 can be used to scan or otherwise input the identifying information provided by labels 66. As used herein, identifying labels 66 may take any number of different forms. In other words any physical embodiment of information can be a label as used herein. The interferometric image data acquired for each oocyte/COC is associated with the identifying label/information for that oocyte/COC so that the maturity assessment which relies upon the image data can be applied to the proper oocyte/COC.

The performance of an oocyte/COC assessment will now be described. The items used to perform such an assessment, in addition to the equipment discussed above, will generally include gloves, beaker, razor, 80% ethanol spray bottle, tips, pipettes, media, and mineral oil.

In preparation for the test, chamber 90 is cleaned. The chamber is advantageously sprayed with 80% ethanol spray and then wiped out. The chamber 90 is then subjected to ultraviolet (UV) light for 10 minutes. Both the temperature and the $CO_2$ level of chamber are then checked to ensure that they are within an acceptable range.

System 20 and associated software is then energized. A mask sample is used to adjust the focus of the image range and validate that system 20 is operating correctly. A mask sample is a three-dimensional printed card with different size three-dimensional text. It is used to find the focal plane of both the white/red light image acquired with sensor 50 and the interferometric image acquired with detector 46. The mask sample is also used to path match the reference and signal beams of the SLD light. If the validation step is successful, the process continues, otherwise, the process is stopped to determine and fix the problem.

The petri dish used in the imaging is then prepared using medium and mineral oil. An individual sealed petri dish is opened and medium is applied in the center of the petri dish. Then, mineral oil is slowly introduced until it covers the center medium. The petri dish cover is kept on after preparation of the petri dish with medium and mineral oil and the imaging petri dish is placed on the target support or other location where it will be imaged.

To perform the image, a COC is carefully pipetted from a storage petri dish into the center bottom of the imaging petri dish. The barcode on the storage petri dish is scanned to name the image file that will be collected or otherwise associate the identifying information provided by the barcode with the image data that will be acquired. The white or red LED 52 is energized to refine the focus of the probe 22.

The ROI of the image is then selected. The ROI advantageously encompasses the full COC. Blank background areas are not needed within the ROI. After selecting the ROI, the white/red LED 52 is de-energized.

SLD 30 is then energized and a final focus adjustment can be done on the real time image if necessary. The collection of interferometric image data is then started with a user-input device, e.g., by clicking an appropriate selection with a mouse of the personal computer 26.

During the imaging process, it is advisable not to touch or disturb any of the equipment to avoid unnecessary vibration and movement that might disturb the acquisition of the interferometric image data. After the image data is acquired, the system will de-energize the SLD and advantageously indicate that it has completed acquiring the image data by turning off or providing some other notification, e.g., an audible beep or flash of a light, to inform the embryologist that the imaging is complete.

The COC is then carefully pipetted back to the storage petri dish. The interferometric image data is then uploaded to the cloud or other appropriate location for assessment. This process is repeated until all of the oocytes/COCs are imaged.

As discussed above, the analysis of the image data can happen simultaneously with the acquisition of the images. As soon as the image data is uploaded to cloud, an algorithm can automatically perform an initial assessment and categorize the image data as one of three groups: negative, positive and hard to determine. The back-end embryologist can then examine the image files. It is thought that the most efficient method for such follow-up assessments would first process the positive group, then the negative group and finally the hard to determine group to thereby make final determinations as to whether or not the oocytes/COCs are mature. It is envisioned that within 5 minutes of completing the imaging process, the front-end embryologist will have a list of the imaged COCs together with the assessment as to whether or not the oocyte/COC is mature. The list can identify the individual oocytes/COCs using the identifying information contained on the barcode or other identifying label.

Following the imaging and assessment, the embryologist carefully pipettes the oocytes/COCs from their storage petri-dishes to the desired places. For example, the mature oocytes/COCs can be stored separately from the immature oocytes/COCs. Barcodes on the storage petri-dishes and the barcode/identifying label information on the mature/immature list are used to identify each COC.

While this invention has been described as having an exemplary design, the present invention may be further modified within the spirit and scope of this disclosure. This application is therefore intended to cover any variations, uses, or adaptations of the invention using its general principles.

What is claimed is:

1. A method for non-invasively assessing the maturity of an oocyte, the method comprising:

placing the oocyte in a sample holder to provide a biological target;
generating a near infrared light with a light source, wherein the light source is a superluminescent diode and the near infrared light generated by the light source has a wavelength within the range of 800 micrometers to 1000 micrometers;
using a beam splitter to split the near infrared light into a signal light portion and a reference light portion;
projecting the signal light portion of the near infrared light onto the biological target;
wherein the near infrared light generated by the light source has a power of no more than 5 milliwatts and the step of projecting the signal light portion of the near infrared light onto the biological target exposes the biological target to no more than 100 millijoules of energy from the near infrared light;
collecting reflected and back scattered light from the signal light portion projected onto the biological target with a detector;
collecting at least a portion of the reference light portion with the detector wherein the collected reference light has not interacted with the biological target;
generating interferometric image data based upon the collected signal and reference light;
assessing the maturity of the oocyte based upon the interferometric data while maintaining the viability of the oocyte;
providing an objective lens in the path of the signal light between the beam splitter and the biological target; and
providing a pair of galvanometric mirrors which are controllably rotated about a pair of mutually perpendicular axes and positioning the galvanometric mirrors in the path of the signal light between the beam splitter and the objective lens whereby controlled rotation of the galvanometric mirrors can be used to scan the biological target with the signal light.

2. The method of claim 1 wherein the oocyte forming the biological target is part of a cumulus-oocyte complex and the step of assessing of the maturity of the oocyte is accomplished without denuding cumulus cells from the cumulus-oocyte complex while maintaining the viability of the cumulus-oocyte complex.

3. The method of claim 1 wherein the near infrared light generated by the light source has a wavelength of 850 micrometers.

4. The method of claim 1 wherein the superluminescent diode is coupled with a fiber optic cable and the method further comprises using the fiber optic cable to convey the near infrared light from the superluminescent diode to a location where the light is projected at the beam splitter.

5. The method of claim 4 wherein the superluminescent diode and driving circuitry providing the superluminescent diode with an electrical current to generate the near infrared light are positioned in a first housing that is spaced from and separated from a probe housing, the beam splitter and detector being disposed within the probe housing and wherein the fiber optic cable extends from the first housing to the probe housing and wherein the first housing includes a cooling fan and the probe housing does not include a cooling fan.

6. A method for non-invasively assessing the maturity of an oocyte, the method comprising:

placing the oocyte in a sample holder to provide a biological target;
generating a near infrared light with a light source, wherein the light source is a superluminescent diode and the near infrared light generated by the light source has a wavelength within the range of 800 micrometers to 1000 micrometers;

using a beam splitter to split the near infrared light into a signal light portion and a reference light portion;

projecting the signal light portion of the near infrared light onto the biological target;

wherein the near infrared light generated by the light source has a power of no more than 5 milliwatts and the step of projecting the signal light portion of the near infrared light onto the biological target exposes the biological target to no more than 100 millijoules of energy from the near infrared light;

collecting reflected and back scattered light from the signal light portion projected onto the biological target with a detector;

collecting at least a portion of the reference light portion with the detector wherein the collected reference light has not interacted with the biological target;

generating interferometric image data based upon the collected signal and reference light;

assessing the maturity of the oocyte based upon the interferometric data while maintaining the viability of the oocyte; and providing a second image sensor for recording two-dimensional image data.

7. The method of claim 6 further comprising the step of providing an objective lens in the path of the signal light between the beam splitter and the biological target.

8. The method of claim 6 further comprising the step of providing a pair of galvanometric mirrors which are controllably rotated about a pair of mutually perpendicular axes and positioning the galvanometric mirrors in the path of the signal light between the beam splitter and the objective lens whereby controlled rotation of the galvanometric mirrors can be used to scan the biological target with the signal light.

9. The method of claim 6 wherein a plurality of biological targets are assessed, the plurality of biological targets being disposed in a plurality of sample holders wherein each individual sample holder has an identifying label affixed thereto, and wherein the method further comprises acquiring an image of the identifying label with the second image sensor when assessing a biological target from the sample holder.

10. The method of claim 6 further comprising the step of providing an objective lens in the path of the signal light between the beam splitter and the biological target and positioning the second image sensor to acquire two-dimensional image data of the biological target through the objective lens.

11. The method of claim 1 further comprising:
mounting the objective lens, the beam splitter and the detector in a probe housing;
positioning the sample holder on a target support; and
providing a support structure wherein the probe housing is securable to the support structure at a plurality of different locations whereby the signal light can be directed at the biological target from a plurality of different positions.

12. A system for non-invasively assessing the maturity of an oocyte, the system comprising:
a superluminescent diode which generates a near infrared light having a wavelength within the range of 800 micrometers to 1000 micrometers;
a beam splitter positioned to divide the near infrared light and thereby generate a signal light portion and a reference light portion, the signal light portion being directed at a biological target to generate reflected and back scattered signal light;
a reference beam reflector positioned to reflect the reference light portion;
a detector positioned to receive the reference light portion reflected by the reference beam reflector and the reflected and back scattered signal light to thereby generate interferometric image data of the biological target;
a pair of galvanometric mirrors controllably rotatable about mutually perpendicular axes wherein the galvanometric mirrors are positioned in the path of the signal light portion between the beam splitter and the biological target; and
an objective lens positioned in the path of the signal light portion between the pair of galvanometric mirrors and the biological target.

13. The system of claim 12 wherein the near infrared light generated by the superluminescent diode has a wavelength of 850 micrometers.

14. The system of claim 12 wherein the superluminescent diode is coupled with a fiber optic cable, the fiber optic cable conveying the near infrared light generated by the superluminescent diode to a location where the light is projected at the beam splitter.

15. The system of claim 14 wherein the near infrared light generated by the superluminescent diode has a power of no more than 5 milliwatts as conveyed through the fiber optic cable.

16. The system of claim 14 further comprising driving circuitry which supplies electrical current to drive the operation of the superluminescent diode, the driving circuitry and the superluminescent diode being disposed in a first housing, the beam splitter, the reference beam reflector and the detector being disposed in a probe housing, the probe housing being separate and spaced apart from the first housing, the fiber optic cable conveying the near infrared light extending between the first housing and the probe housing and emitting the near infrared light within the probe housing.

17. A system for non-invasively assessing the maturity of an oocyte, the system comprising:
a superluminescent diode which generates a near infrared light having a wavelength within the range of 800 micrometers to 1000 micrometers;
a beam splitter positioned to divide the near infrared light and thereby generate a signal light portion and a reference light portion, the signal light portion being directed at a biological target to generate reflected and back scattered signal light;
a reference beam reflector positioned to reflect the reference light portion;
a detector positioned to receive the reference light portion reflected by the reference beam reflector and the reflected and back scattered signal light to thereby generate interferometric image data of the biological target and
a second image sensor adapted to record two-dimensional image data.

18. The system of claim 17 wherein the system further comprises:
a pair of galvanometric mirrors controllably rotatable about mutually perpendicular axes wherein the galvanometric mirrors are positioned in the path of the signal light portion between the beam splitter and the biological target; and an objective lens positioned in the path of the signal light portion between the pair of galvanometric mirrors and the biological target.

19. The system of claim 17 further comprising a plurality of sample holders, each sample holder being adapted to hold a separate biological target and wherein each sample holder has an identifying label affixed thereto, and wherein the second image sensor is adapted to acquire an image of the identifying label on the sample holder.

20. The system of claim 17 further comprising an objective lens positioned between the beam splitter and the biological target and a second light source positioned to illuminate the biological target and wherein the second image sensor is positioned to collect light generated by the second light source after the light generated by the second light source has interacted with the biological target and passed through the objective lens to thereby acquire image data of the biological target.

21. The system of claim 12 further comprising a probe housing and an objective lens wherein the beam splitter, reference beam reflector, objective lens and detector are disposed on the probe housing and wherein the objective lens is positioned in the path of the signal light portion between the beam splitter and the biological target; and
- a support structure, the support structure comprising a support ring and a target support, the biological target being supportable on the target support, and wherein the probe housing is securable to the support ring at a plurality of different location encircling the target support whereby the signal light can be directed at the biological target from a plurality of different positions.

* * * * *

UNITED STATES PATENT AND TRADEMARK OFFICE
CERTIFICATE OF CORRECTION

| | | |
|---|---|---|
| PATENT NO. | : 11,644,424 B2 | Page 1 of 1 |
| APPLICATION NO. | : 16/859537 | |
| DATED | : May 9, 2023 | |
| INVENTOR(S) | : Ran An et al. | |

It is certified that error appears in the above-identified patent and that said Letters Patent is hereby corrected as shown below:

On the Title Page

Item (72) ADD - Brian A Levine, MD, MS, New York, NY (US) -

Signed and Sealed this
Fifteenth Day of April, 2025

Coke Morgan Stewart
*Acting Director of the United States Patent and Trademark Office*